(12) United States Patent
Strayer (10) Patent No.: US 12,016,992 B2
(45) Date of Patent: Jun. 25, 2024

(54) SURGICAL HANDPIECE FOR OCULAR SURGERY

(71) Applicant: Johnson & Johnson Surgical Vision, Inc., Irvine, CA (US)

(72) Inventor: Scott Strayer, Rancho Santa Margarita, CA (US)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 272 days.

(21) Appl. No.: 17/330,260

(22) Filed: May 25, 2021

(65) Prior Publication Data

US 2021/0393869 A1 Dec. 23, 2021

Related U.S. Application Data

(60) Provisional application No. 63/041,738, filed on Jun. 19, 2020.

(51) Int. Cl.
*A61M 1/00* (2006.01)
*A61F 9/007* (2006.01)
*A61M 3/02* (2006.01)

(52) U.S. Cl.
CPC ......... *A61M 1/774* (2021.05); *A61F 9/00745* (2013.01); *A61M 1/772* (2021.05);
(Continued)

(58) Field of Classification Search
CPC ........ A61M 1/77; A61M 1/772; A61M 1/774; A61M 1/777; A61M 1/84; A61M 1/842; A61M 1/85; A61M 1/92; A61M 1/0023; A61M 1/0062; A61M 2/0283; A61M 3/0233; A61M 3/0245; A61F 9/007; A61F 9/00745; A61F 9/00736; A61B 2217/005;
(Continued)

(56) References Cited

U.S. PATENT DOCUMENTS

| 3,034,809 A | 5/1962 | Jay et al. |
| 4,138,751 A | 2/1979 | Kentosh |

(Continued)

FOREIGN PATENT DOCUMENTS

| EP | 1464311 A1 | 10/2004 |
| EP | 2539221 A1 | 1/2013 |
| WO | 2020021397 A1 | 1/2020 |

*Primary Examiner* — Leslie A Lopez
*Assistant Examiner* — Timothy L Flynn
(74) *Attorney, Agent, or Firm* — Johnson & Johnson Surgical Vision, Inc.

(57) ABSTRACT

An apparatus, system and method for a handpiece for ocular surgical. Included may be at least: a proximal portion having at least inlet ports for irrigation tubing and aspiration tubing, and providing an irrigation fluidic pathway extending therethrough from the irrigation tubing inlet port, and an aspiration fluidic pathway extending therethrough from the aspiration inlet port; a distal portion terminating in an emulsifying tip, and providing an aspiration pathway terminating in an aspiration output, and at least one irrigation pathway terminating in at least one irrigation output; and a swivel ball provided at a base of the proximal portion and having a first opening to the irrigation fluidic pathway, and a second opening to the aspiration fluidic pathway, which seats within a socket cup provided at an upper end of the distal portion.

18 Claims, 6 Drawing Sheets

(52) U.S. Cl.
CPC ........ *A61M 3/0233* (2013.01); *A61M 3/0283* (2013.01); *A61B 2217/005* (2013.01); *A61B 2217/007* (2013.01)

(58) Field of Classification Search
CPC ...... A61B 2217/007; A61B 2017/2908; A61B 2017/2927; A61B 2017/2929; A61B 17/32007; A61B 2018/00202; A61B 2018/00208
See application file for complete search history.

(56) References Cited

U.S. PATENT DOCUMENTS

| | | | |
|---|---|---|---|
| 4,447,226 A * | 5/1984 | Mayoral | A61M 1/75 604/32 |
| 4,875,718 A | 10/1989 | Marken | |
| 5,350,356 A * | 9/1994 | Bales | A61M 3/022 604/27 |
| 5,797,413 A | 8/1998 | Pollack | |
| 7,473,263 B2 * | 1/2009 | Johnston | A61B 34/74 604/35 |
| 2008/0033348 A1* | 2/2008 | Bidoia | A61M 3/0258 604/35 |
| 2009/0018539 A1 | 1/2009 | Cosmescu | |
| 2010/0069825 A1 | 3/2010 | Raney | |
| 2012/0157788 A1* | 6/2012 | Serowski | A61B 90/50 600/229 |
| 2013/0164706 A1 | 6/2013 | Odabashian et al. | |
| 2015/0157501 A1 | 6/2015 | Bourne et al. | |
| 2015/0202424 A1 | 7/2015 | Harton | |
| 2016/0161036 A1 | 6/2016 | Randrianarivony | |
| 2017/0367885 A1* | 12/2017 | Bourne | A61M 1/80 |
| 2018/0353179 A1* | 12/2018 | Shelton, IV | A61B 17/068 |
| 2020/0069468 A1 | 3/2020 | Litherland et al. | |
| 2020/0306082 A1* | 10/2020 | Jimenez Onofre | A61M 1/00 |
| 2021/0068917 A1* | 3/2021 | Ryan | A61B 17/3462 |

* cited by examiner

SURGICAL HANDPIECE FOR OCULAR SURGERY

CROSS-REFERENCE TO RELATED APPLICATIONS

This application claims the benefit under 35 U.S.C. § 119(e) of U.S. Provisional Patent Application No. 63/041,738, filed Jun. 19, 2020, which is incorporated herein by reference in its entirety.

FIELD OF THE DISCLOSURE

The disclosure relates to medical instruments, and more specifically, to a surgical handpiece for performing ocular surgery.

BACKGROUND

A cataract is a type of visual impairment and is defined as an opacity in the crystalline lens of the eye which interferes with vision. Once visual function has been compromised by a cataract, surgery is performed to remove the opaque lens in order to restore proper eye function. Cataracts are the most prevalent disabling eye disease worldwide.

Many methods of cataract extraction have been developed. Some of these methods require large incisions that are unstable and require prolonged recovery times. More current techniques generally require making much smaller incisions in the eye and removing the cataract from the eye through this small incision. Smaller incisions, of course, result in more rapid post-operative recovery and a more structurally stable eye. Thus, the presently preferred surgical method of cataract extraction is extracapsular removal, such as by extracapsular surgery or phacoemulsification, through a very small incision.

More specifically, surgeries today typically involve making a very small incision (2-7 mm) in the eye, and either removing the cataractous nucleus intact or emulsifying/fragmenting the nucleus and mechanically removing the pieces through the incision. As referenced above, smaller incision sizes are preferable for a variety of reasons, although the smaller the incision the greater the fragmentation of the cataract that is required to remove it from the eye through the incision, and the smaller and more ergonomic the removal in strum ent must be.

Yet more particularly, a phacoemulsification handpiece typically utilizes ultrasonic energy to emulsify a cataract nucleus. Of note, the advent of foldable intraocular lenses to complete this surgery has resulted in sutureless surgery using the referenced small incision, through which the ultrasonic handpiece is inserted prior to insertion of the foldable lens, with virtually immediate visual and functional recovery. For these and other reasons, phacoemulsification has become the most practiced method of cataract surgery.

A typical handpiece in the known art not only includes the aforementioned vibrating ultrasonic phacoemulsification tip, but additionally includes irrigation and aspiration lines. The aspiration provides a vacuum to remove the emulsified lens, and the irrigation provides liquid to flow the emulsified pieces from the eye and to maintain pressure within the eye.

More particularly, current phacoemulsification handpieces generally use a rigid tube, such as a titanium tube, that terminates in the vibrating Phacoemulsification tip. The rigid tube typically includes the irrigation and aspiration lines running therethrough, from the proximal end thereof, at which the flow feed lines for the irrigation and aspiration associate with the hand piece, to the distal end thereof, which terminates in the phacoemulsification tip.

During a typical phacoemulsification procedure, this rigid tube must be lifted and rotated, along with its associated tubing, to reach all areas of the eye through the referenced incision during the irrigation and aspiration phase. This need to lift and rotate both the tubing lines associated with the handpiece, and the handpiece itself, often results in hand and forearm fatigue for the surgeon, along with general inconvenience and enhanced surgical difficulty. Because of this, surgeons often wrap at least the aspiration and irrigation tubing lines around their respective forearm or hand, in an attempt to thereby reduce hand and forearm fatigue and strain.

The aforementioned poor ergonomics of the tubing associated with the handpiece are problematic both during and after the phacoemulsification portion of a procedure. For example, during the phacoemulsification portion, although there is nota heightened need for the surgeon to be able to reach the handpiece to all areas of the eye, the tubing lines associated with the hand piece nevertheless limit the surgeon's range of motion in using the phacoemulsification tip. Of course, this issue is exacerbated after the phacoemulsification phase, as referenced above, at which time the need to reach all areas of the eye with irrigation and aspiration from the distal end of the handpiece is heightened.

Current handpieces often employ the rigid titanium referenced above, or similar metal or plastic rigid handpiece bodies, along with a series of molded or machined fittings. It is typical that these fittings are at the proximal end of the hand piece, and allow for connection of the handpiece to the tubing packs for the irrigation and aspiration. However, at present, none of these fittings enable ergonomic movement of the handpiece attached to the fittings, as discussed above.

For at least the foregoing reasons, there is a need for an ocular surgery handpiece that provides improved ergonomics in relation to movement of the handpiece by a surgeon, preferably while also decreasing the fatigue and inconvenience to the surgeon.

SUMMARY OF THE DISCLOSURE

The disclosure includes at least an apparatus, system and method for a handpiece for ocular surgical. The apparatus, system and method may include at least: a proximal portion having at least inlet ports for irrigation tubing and aspiration tubing, and providing an irrigation fluidic pathway extending therethrough from the irrigation tubing inlet port, and providing an aspiration fluidic pathway extending therethrough from the aspiration inlet port; a distal portion terminating in an emulsifying tip, and providing an aspiration pathway terminating in an aspiration output, and at least one irrigation pathway terminating in at least one irrigation output; and a swivel ball provided at a base of the proximal portion and having a first opening to the irrigation fluidic pathway, and a second opening to the aspiration fluidic pathway, which seats within a socket cup provided at an upper end of the distal portion, wherein the socket cup provides an irrigation opening that fluidically connects the first opening and the at least one irrigation pathway, and an aspiration opening that fluidically connects the second opening and the aspiration pathway.

The swivel ball may be capable of both an axial angular rotation and a circumferential rotation within the socket cup. These rotations may occur while maintaining continuous fluidic communication from the irrigation tubing inlet port to the at least one irrigation output, and from the aspiration tubing inlet port to the aspiration output.

Thus, the disclosure may provide an ocular surgery handpiece that provides improved ergonomics in relation to movement of the handpiece by a surgeon, and that also decreases the fatigue and inconvenience to the surgeon.

BRIEF DESCRIPTION OF THE DRAWINGS

The accompanying drawings are included to provide a further understanding of the disclosure and are incorporated into and thus constitute a part of this specification. The drawings illustrate disclosed embodiments and/or aspects and, together with the description, serve to explain the principles of the disclosure. In the drawings.

DETAILED DESCRIPTION

The figures and descriptions provided herein may be simplified to illustrate aspects of the described embodiments that are relevant fora clear understanding of the herein disclosed processes, machines, manufactures, and/or compositions of matter, while eliminating, for the purpose of clarity, other aspects that may be found in typical surgical, and particularly ophthalmic surgical, devices, systems, and methods. Those of ordinary skill may thus recognize that other elements and/or steps may be desirable or necessary to implement the devices, systems, and methods described herein. Because such elements and steps are well known in the art, and because they do not facilitate a better understanding of the disclosed embodiments, a discussion of such elements and steps may not be provided herein. However, the present disclosure is deemed to inherently include all such elements, variations, and modifications to the described aspects that would be known to those of ordinary skill in the pertinent art.

Embodiments are provided throughout so that this disclosure is sufficiently thorough and fully conveys the scope of the disclosed embodiments to those who are skilled in the art. Numerous specific details are set forth, such as examples of specific aspects, devices, and methods, to provide a thorough understanding of embodiments of the present disclosure. Nevertheless, it will be apparent to those skilled in the art that certain specific disclosed details need not be employed, and that embodiments may be embodied in different forms. As such, the exemplary embodiments set forth should not be construed to limit the scope of the disclosure.

The terminology used herein is for the purpose of describing particular embodiments only and is not intended to be limiting. For example, as used herein, the singular forms "a", "an" and "the" may be intended to include the plural forms as well, unless the context clearly indicates otherwise. The terms "comprises," "comprising," "including," and "having," are inclusive and therefore specify the presence of stated features, steps, operations, elements, and/or components, but do not preclude the presence or addition of one or more other features, steps, operations, elements, components, and/or groups thereof. The steps, processes, and operations described herein are not to be construed as necessarily requiring their respective performance in the particular order discussed or illustrated, unless specifically identified as a preferred or required order of performance. It is also to be understood that additional or alternative steps may be employed, in place of or in conjunction with the disclosed aspects.

When an element or layer is referred to as being "on", "upon", "connected to" or "coupled to" another element or layer, it may be directly on, upon, connected or coupled to the other element or layer, or intervening elements or layers may be present, unless clearly indicated otherwise. In contrast, when an element or layer is referred to as being "directly on," "directly upon", "directly connected to" or "directly coupled to" another element or layer, there may be no intervening elements or layers present. Other words used to describe the relation ship between elements should be interpreted in a like fashion (e.g., "between" versus "directly between," "adjacent" versus "directly adjacent," etc.). Further, as used herein the term "and/or" includes any and all combinations of one or more of the associated listed items.

Yet further, although the terms first, second, third, etc. may be used herein to describe various elements or aspects, these elements or aspects should not be limited by these terms. These terms may be only used to distinguish one element or aspect from another. Thus, terms such as "first," "second," and other numerical terms when used herein do not imply a sequence or order unless clearly indicated by the context. Thus, a first element, component, region, layer or section discussed below could be termed a second element, component, region, layer or section without departing from the teachings of the disclosure.

In light of the aforementioned issues with known phacoemulsification handpieces, the embodiments provide a reservoir-based, dual passage system which provides two passages through a swivel mechanism that is integrated into or coupled with a phacoemulsification handpiece or the like, e.g. an irrigation/aspiration handpiece or vitrectomy handpiece. In accordance with the embodiments, the need to move and restrain the irrigation and aspiration tubing lines feeding the handpiece may be decoupled from the rotation and angular movement of the handpiece, as discussed throughout. This decoupling may allow for the tubing lines to simply rest across the back of the surgeon's hand or forearm, for example, without the unnecessary fatigue to the surgeon that occurs in the known art during a phacoemulsification procedure.

More particularly, the disclosed dual passage swivel mechanism uses a series of cylindrical passageways to seal off aspiration and irrigation lines from one another, while maintaining the potential for irrigation fluid flow into the eye and vacuum during aspiration. Moreover, the disclosed swivel mechanism integrates one or more removable retaining and sealing rings, which may readily allow for cleaning and re-sterilization of the disclosed handpiece by surgical staff.

In the embodiments, the swivel mechanism may allow for a tilt angle in a range of, for example, 10 to 30°, or, more particularly, about 28°, of the proximal end of the phacoemulsification handpiece with respect to the distal end. Of course, it will be appreciated by the skilled artisan that a tilt angle of up to 90° may be achieved in accordance with the disclosure, but that the size and weight of the swivel mechanism discussed throughout will necessarily increase in proportion to an increase in tilt angle. Yet further, because the tilt mechanism is provided in the embodiments in conjunction with swivel capability, the disclosed proximal end of the phacoemulsification hand piece may also be enabled to rotate in a range of 180 degrees up to 360° circumferentially/coaxially with respect to the distal-most portion of the hand piece, thereby allowing for easy movement of the hand piece with respect to the attached tubing lines without unnecessary fatigue to the surgeon.

Figure 1:
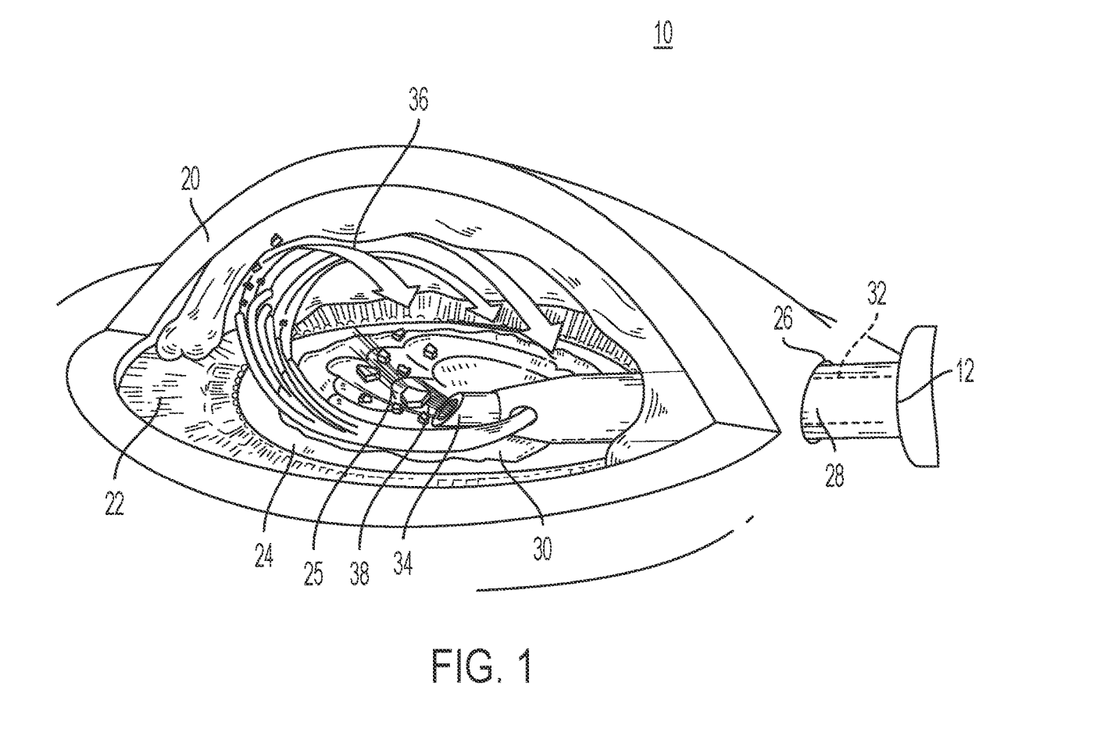
FIG. 1 is a cross-sectional view of an eye subjected to phacoemulsification surgery.

With reference now to FIG. 1, a cornea 20 of a human eye 10 is illustrated. The cornea 20 is a generally arcuate segment in front of the iris 22. The region between the iris and the cornea 20 is known as the anterior chamber of the eye. Directly behind the iris 22 is a lens capsule 24, and, in a healthy eye, a natural crystalline convex lens 25 is housed within the capsule 24 for focusing light, in cooperation with the cornea 20, upon the retina (not shown).

Through trauma, age or other causes, the natural crystalline lens 25 may become cloudy and fail to transmit and focus light in a proper manner. When this condition exists, a patient is said to have a "cataract," and the patient may become progressively functionally blind in the eye suffering from the cataract. Cataracts are a leading cause of blindness throughout the world, but a cataractous lens may be removed and replaced with an artificial intraocular lens to at least partially restore sight.

A currently preferred technique for removing a cataract lens is known as phacoemulsification, and this technique employs irrigation and aspiration in conjunction with the emulsification of the affected lens 25 via ultrasound. In phacoemulsification, an opening 26 is surgically fashioned through the limbus or clear cornea portion of the eye. This opening serves to admit the tip of a phacoemulsification handpiece 12 and/or irrigation and aspiration handpiece (not shown) or other handpiece used in such surgery, e.g. vitrectomy and diathermy handpieces (not shown). The operative end 28 of the handpiece is operably extended through the cornea and into juxtaposition with cataractous lens 25.

In a conventional phacoemulsification, an electromagnetic core 32 internal to the phacoemulsification handpiece 12 is ultrasonically excited from a power source. The core rapidly vibrates at between 10,000 and 100,000 cycles per second, for example. This rapid ultrasonic vibration serves to vibrate a needle or tip 34 of the handpiece, which is brought into physical contact with the cataractous lens 25. The rapidly vibrating tip of needle 34 emulsifies the cataract.

Concomitantly, an irrigation fluid 36 is supplied by the handpiece to commingle with and operably suspend bits of the emulsified cataract within, and further to maintain an acceptable pressure within, the anterior chamber. A vacuum 38 is also drawn by the handpiece, which serves to pull the irrigating fluid and suspended cataract material co-axially through the needle 34 and into a collection reservoir of a surgical console (not shown).

Figure 2:
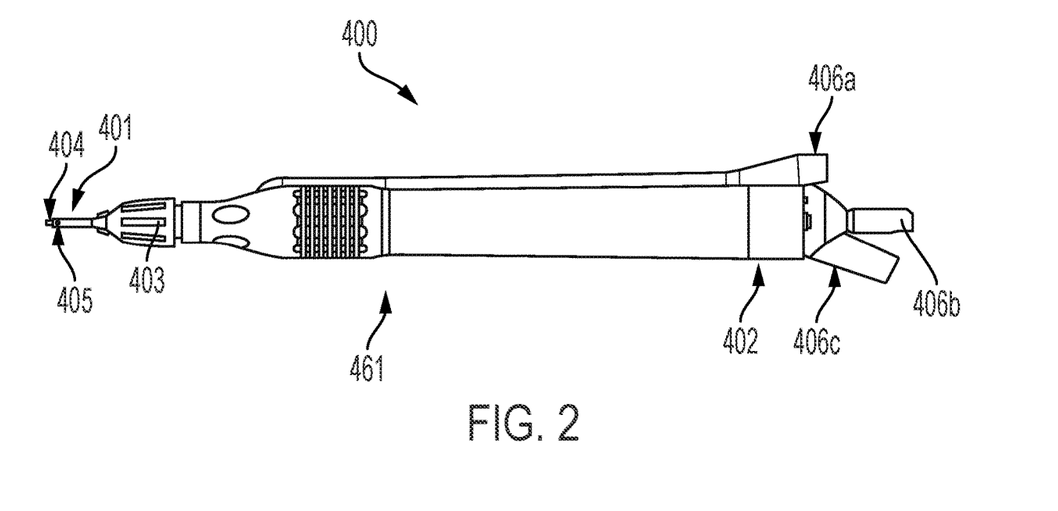
FIG. 2 is an illustrative view of an exemplary ocular surgical instrument.

In FIG. 2, an exemplary phacoemulsification handpiece that may b e used with the present invention is illustrated. The handpiece 400 may have a handle 461 with a distal end 401 having a needle/tip 404 at least partially surrounded by sleeve 403. The hand piece 400 may include, such as passing through the handle thereof, one or more inlets, outlets, and connections 406a, b, c, such as may be associated with the providing of irrigation, aspiration, and/or power from the proximal end 402 of the handpiece to or near to the emulsifying tip at the distal end 401 where the emulsification may occur.

In the illustration, irrigation may outflow from one or more ports 405 located in sleeve 403 as illustrated, such as via fluidic communication between port(s) 405 and the one or more inlets and outlets 406a and b, as shown as passing through or connecting to the handle 461. Power may be provided to the handpiece via power connection 406c. Other fluidics, such as including the aspiration for the cataractous lens, may also flow through or along an internal b ore from emulsifying distal end 401 through handle 461, and may thus likewise stem from the inlets/outlets 406a, 406b. Thereby, particles of the lens, such as including the cataract, may, during and after emulsification, be irrigated by the irrigation and aspirated between the distal end 401 and the proximal end 402. For example, maintenance of the requisite eye pressure for the emulsification may be enabled by irrigation that is thus provided, while the aspiration port balances the irrigation fluid with the provided vacuum.

Figure 3:
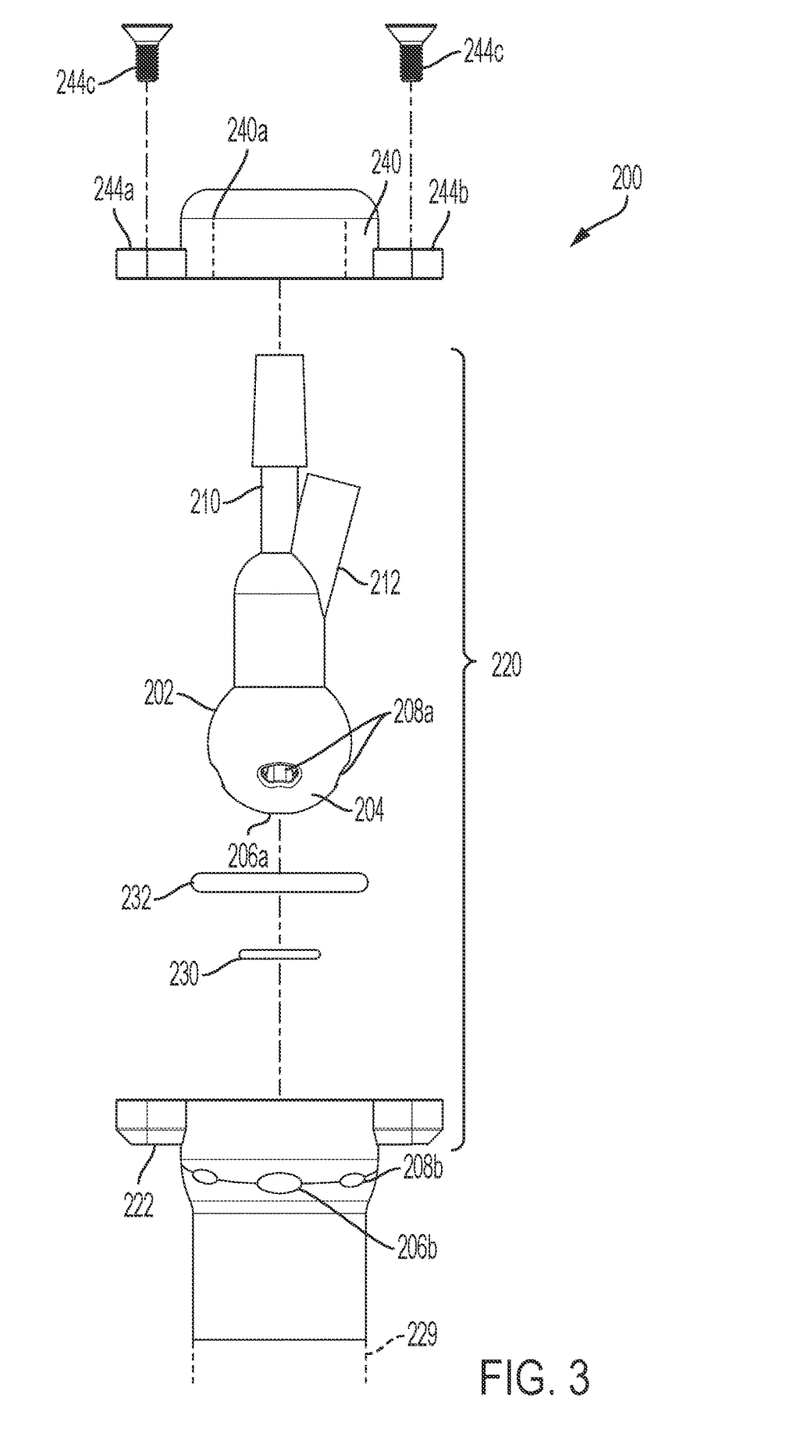
FIG. 3 is an illustrative view of an exemplary ocular surgical instrument.

FIG. 3 shows a breakout view of select components of a swiveling and tilting handpiece portion 200 according to the disclosure. The illustrated handpiece portion 200 includes a swivel ball 202 having, at the base thereof, a spherical portion 204 additionally comprised of at least two port points 206a, 208a passing through the base of the spherical portion 204 and in fluid communication with at least two ports 210, 212 of the proximal portion 220 of the handpiece 200. In an embodiment, one or more of the ports described herein, including those located on swivel ball 202, may have a chamfer 207 at the opening of the ports to help prevent clogging.

The swivel ball 202, and consequently the proximal handpiece portion 220, is rotatably associated with a socket cup 222 having a concave portion suitable to receive the swivel ball 202 at an uppermost portion thereof. In an embodiment, the swivel ball 202 may be made of metal or plastic, or any substantially hard material.

The distal portion 229 of the handpiece 200 terminates in a phacoemulsification tip (not shown) distal from the socket cup 222. In embodiments, the socket cup 222 may provide a substantially uniform, low friction surface to allow for free rotation of the adjoining swivel ball 202. Alternatively, the socket cup 222 may provide alternating higher friction and lower friction surfaces such that the adjoining swivel ball 202 may effectively "click" to various tilt angles as may be tactilely sensed by the operating surgeon. Of note, the socket cup 222 additionally provides at least two port points 206b, 208b passing there through to the distal portion of the hand piece 200, such that irrigation and aspiration may be provided from the input ports 210, 212 on the proximal portion through the swivel ball port points 206a, 208a, and through the socket cup port points 206b, 208b to the distal end of the handpiece 200.

As referenced, the handpiece 200 may additionally include at least two seals 230, 232—one for irrigation and one for aspiration. These seals 230, 232 may be formed of rubber, plastic, silicon, or any other substance suitable to provide an at least a substantially watertight and/or airtight seal. More particularly, the seals 230, 232 disclosed herein may be capable of providing the vacuum required of the aspiration aspect.

In the illustration, the lower seal 230 is provided for aspiration, and, because this lower seal 230 resides in the lower concavity of the socket cup 222, it is smaller in size in the illustrated embodiment. The upper seal 232 in the illustration is provided for irrigation. Because this seal 232 resides in the upper concavity of the socket cup 222, it is larger than the lower seal 230, as shown. It will be appreciated by the skilled artisan in light of the discussion herein that the sizing and location of the irrigation and aspiration seals 230, 232 in association with both the swivel ball 202 and the socket cup 222 may be related to the location of the respective irrigation and aspiration port points 206a, 208a as they exit from the swivel ball 202 and into the socket cup 222.

Also shown is a retainer 240 having an opening 240a passing therethrough, such that the retainer 240 may be placed over the proximal portion 220 of the handpiece 200 to fit relatively snugly about the upper portion of the swivel ball 202, and to effectuate a seal between the retainer 240 and at least a portion of the swivel ball 202 using the upper seal 232. It will b e appreciated that the retainer 240 may also physically affect the uppermost portion of the socket cup 222, such that both of the seals 230, 232 discussed above may be actuated by the downward pressure of the retainer 240.

By way of nonlimiting example, the upper portion of the socket cup 222 may b e threaded on its outside, and the retainer 240 may be matedly threaded on an inner portion thereof, such that the retainer 240 may "thread down" onto the outermost/uppermost portion of the socket cup 222. Alternatively, the socket cup 222 may include, at two or more portions at the uppermost/outermost portion thereof, receiving holes 244a, b for screws or rivets 244c that may pass through those outermost portions of the retainer 240, such that, when the screws or rivets 244c are actuated through the receiving holes 244a, b, the socket cup 222 is firmly mated to the retainer 240. In an embodiment, the screws or rivets 244c provide the ability to more easily clean, sterilize, or service the assembly, e.g. replace a seal/O-ring, if needed. In another embodiment, retainer 240 may connected by locking tabs or any other mechanism for joining two pieces or parts together that also permit unlocking to enable cleaning or servicing. In another embodiment, retainer 240 may be ultrasonically welded preventing separation or any other means of semi-permanent or permanent connection between two pieces or parts may b e used.

Figure 4:
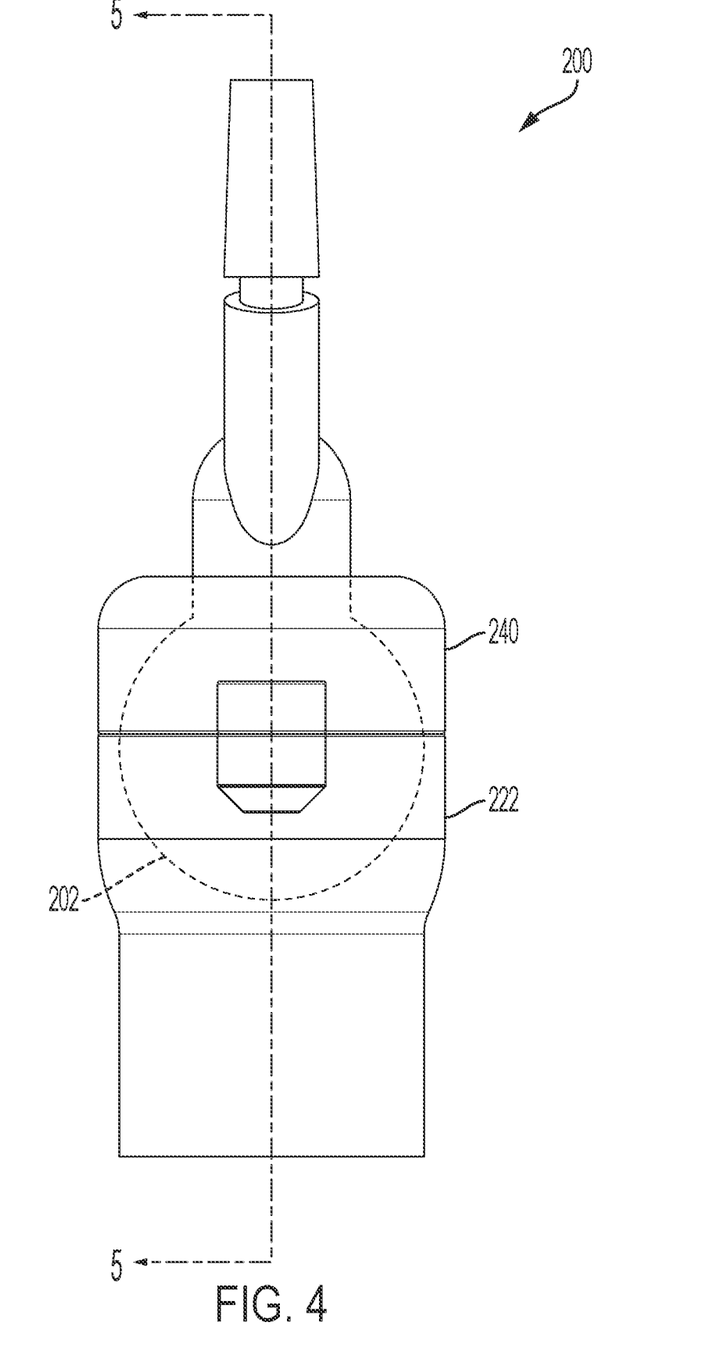
FIG. 4 is an illustrative view of an exemplary ocular surgical instrument.

FIG. 4 illustrates, in profile, the portions of the handpiece 200 discussed above in FIG. 3. Of note, the illustration of FIG. 4 shows the retainer 240 of FIG. 3 mated to the uppermost portion of the socket cup 222, such that the swivel ball 202 and seals (not shown in FIG. 4) discussed in FIG. 3 form a seal between the retainer 240 and the socket cup 222.

Figure 5:
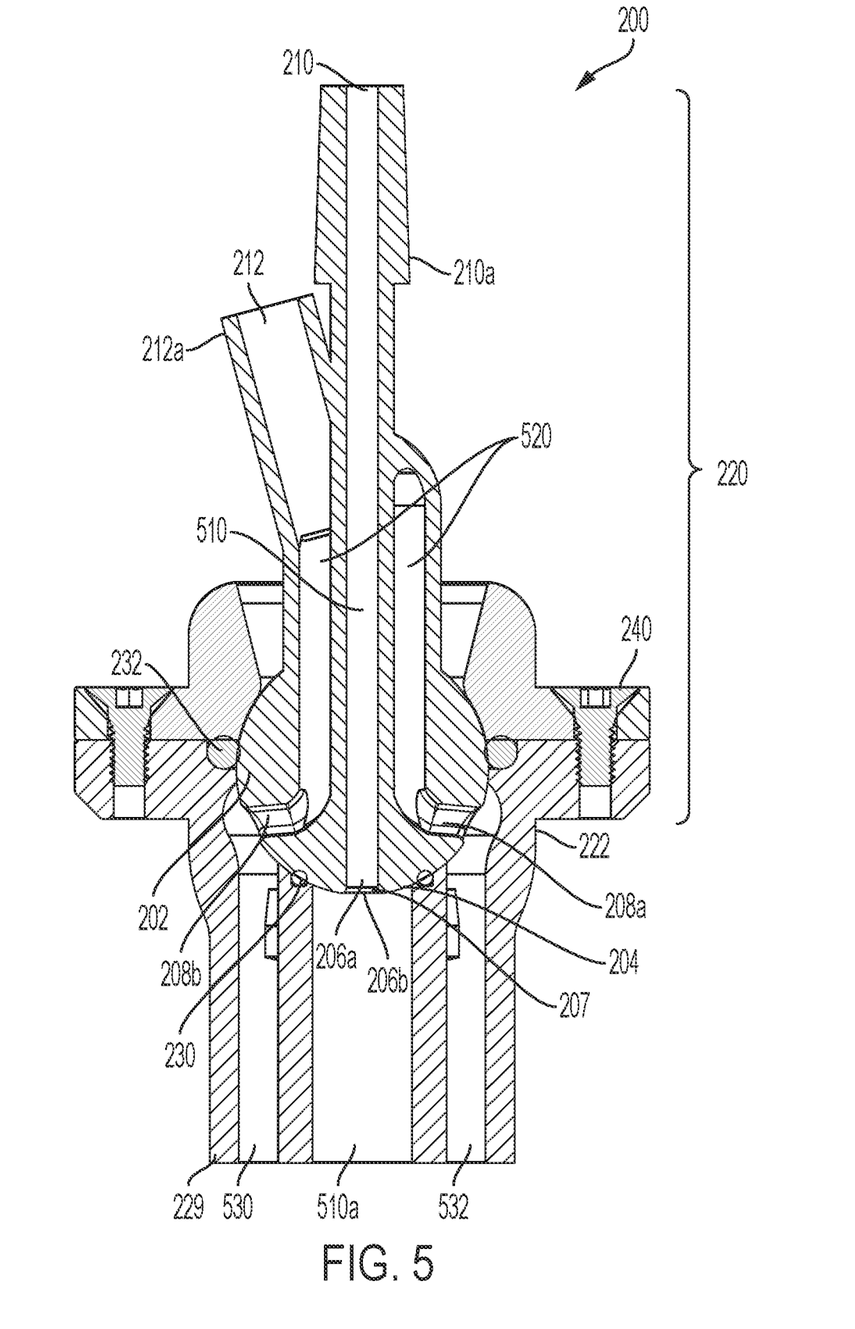
FIG. 5 is an illustrative view of an exemplary ocular surgical instrument.

FIG. 5 illustrates the disclosed handpiece 200 in a cross-sectional view in the coaxial position. As shown, at the proximal portion 220 thereof the handpiece 200 includes both aspiration and irrigation input ports 210, 212. By way of nonlimiting example, the aspiration port connector 210a may be coaxial with the handpiece 200 as illustrated and may comprise a female aspiration Luer connection 210a. The irrigation input 212 may be angularly off-axis with respect to the center access of the handpiece 200 and may comprise a male irrigation luer 212a connection.

In the illustration, the aspiration fluidic line 510 passes centrally through the proximal portion 220, through the swivel ball 202, through the socket cup 222, and into fluidic communication with a central passageway 510a beginning at the base of the socket cup 222 and extending into the distal end of the phacoemulsification handpiece 200. It should also b e noted that, because the swivel ball 202 may rotate within the socket cup 222, the aspiration central passageway 510a may be oversized with respect to the passage 510 passing into/through the swivel ball 202, such that fluidic communication may occur from the swivel ball aspiration p ort points 206a into the socket cup port points 206b through multiple angular positions of the swivel ball 202. Further, it should be noted that the oversized aspiration central pathway 510a starting at the base of the socket cup 222 is preferably substantially sealed to the swivel ball 202 by the aspiration seal 232 discussed above with respect to FIG. 3, and that the seal is maintained through multiple angular rotation positions of the swivel ball 202.

Also evident in FIG. 5 is an irrigation flow reservoir 520 fluidically associated with at least one irrigation flow pathway 530, 532. In short, the irrigation flow reservoir 520 may comprise a substantially circumferential portion about the base of the irrigation input port 212 or may extend downwardly from the input toward the swivel ball 202. In any case, the irrigation flow reservoir 520 thereby provides irrigation fluid to the irrigation flow pathway(s) 530, 532, which may also comprise a single pathway that allows continuous fluid flow at least substantially around the circumference of the distal portion.

As shown, the irrigation flow pathway(s) 530, 532 passes through the proximal portion 220 of the handpiece 200 and the swivel ball 202 for fluidic association with opening(s) to the distal portion irrigation flow passageway(s) starting proximate to the socket cup port points 206b, 208b. It should again be noted that at least the upper portion of, or the entirety of, the lateral distance from the outer wall to the inner-aspiration wall of the irrigation flow passageway(s) 530, 532 through to the distal portion may be oversized (such as while also extending substantially circumferentially) with respect to the port point(s) in the socket ball 202, at least so as to allow for maintenance of the flow during tilting of the socket ball 202 as discussed throughout. It will thus be appreciated that the irrigation flow passageway(s) 530, 532 in the distal portion of the handpiece 200 may comprise individual passageways or may run partially or completely circumferentially around the circumference within the distal portion while extending distally, at least so as to allow for rotation of the swivel ball 202 within the socket cup 222 as discussed throughout while maintaining irrigation flow during such rotation.

Also shown is the irrigation line seal 230 discussed above. Of note, the irrigation line seal 230 compresses against the swivel ball 202 and is actuated by the pressing of the retainer 240 onto the upper portion of the socket cup 222. Further, this irrigation seal 230 is "above" the port points for irrigation to pass through and out of the swivel ball 222. This placement of the irrigation seal 230 may correspond to the available tilt angles of the socket b all 202, such that at maximum tilt, one irrigation passageway port point abuts the irrigation seal 230 such that leakage cannot occur upwardly through the retainer 240, and the other irrigation passageway port point of the swivel ball 202 abuts a similar flow stop such as may be: proximate to the aspiration seal 232; interior to the distal portion of the handpiece 200; and within the socket cup 222.

Figure 6:
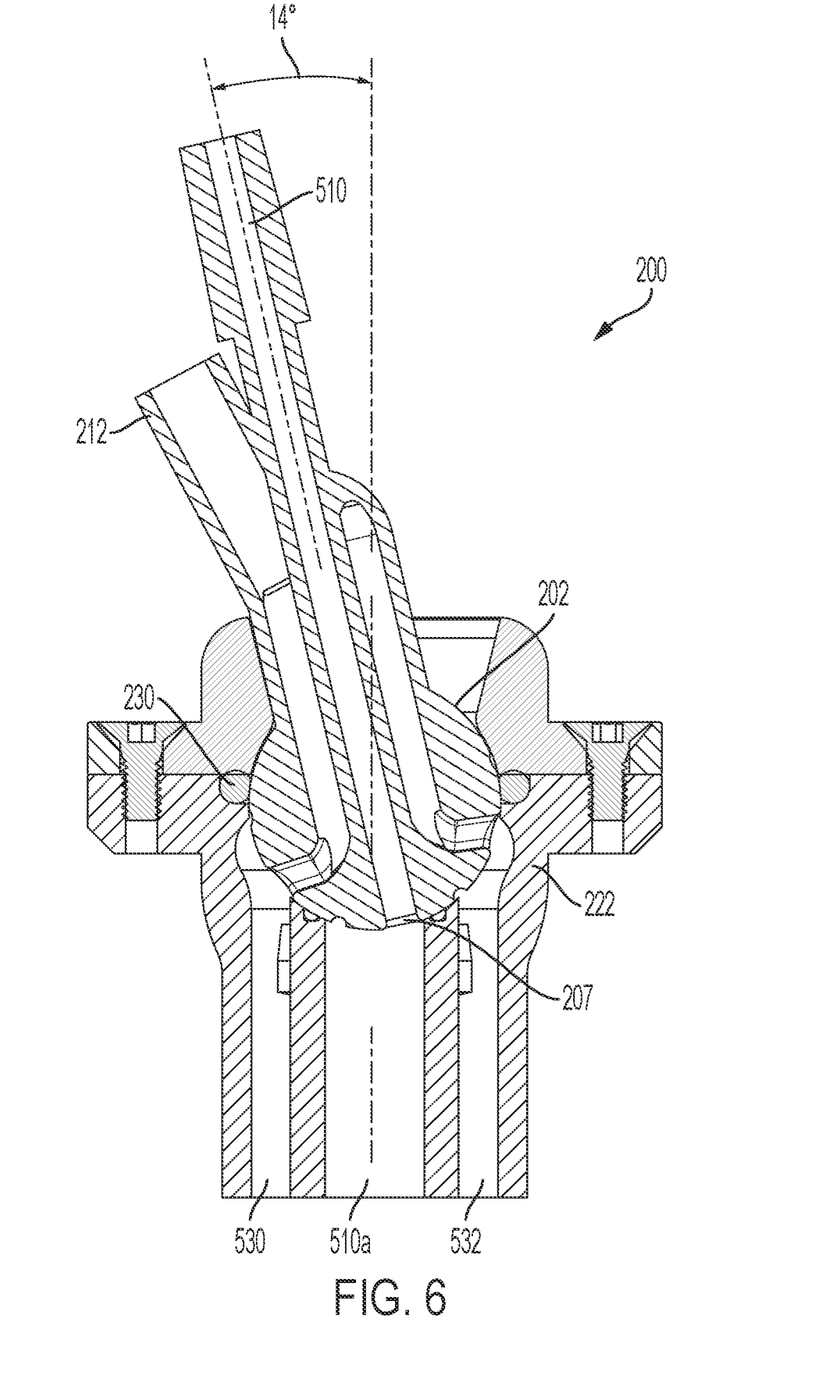
FIG. 6 is an illustrative view of an exemplary ocular surgical instrument.

FIG. 6 illustrates an embodiment of the handpiece 200 of FIG. 5, but with the swivel ball 202 rotating the aspiration port passageway 510 to an approximately 14° tilt position with respect to the central axis of the distal portion of the handpiece 200. In an embodiment, the axial angular rotation of the ball may be from 10 to 90 degrees and in another embodiment, the axial angular rotation of the ball may be from 10 to 30 degrees. As illustrated, aspiration is maintained by a continuous fluid path from the aspiration input 210 to the aspiration pathway 510a in the distal portion of the handpiece 200 and starting at the base of the socket cup 222. Similarly, continuous irrigation flow is maintained from the irrigation input port 212 through to the irrigation pathway(s) 530, 532 in the distal portion of the handpiece 200 matedly associated with the swivel ball 202 at the topmost portion of the socket cup 222. This maintenance of irrigation flow may occur notwithstanding that, as shown, at maximum tilt, the irrigation passageway(s) passing through the swivel ball 202 may abut or be sealed against a portion of the socket cup 222 or the irrigation seal 230.

Although the invention has been described and illustrated in exemplary forms with a certain degree of particularity, it is noted that the description and illustrations have been made by way of example only. Numerous changes in the details of construction, combination, and arrangement of parts and steps may be made. Accordingly, such changes are intended to b e included within the scope of the disclosure.

What is claimed is:

1. A handpiece for ocular surgery, comprising:
   a proximal portion having at least inlet ports for irrigation tubing and aspiration tubing, and providing an irrigation fluidic pathway extending therethrough from the irrigation tubing inlet port, and providing an aspiration fluidic pathway extending therethrough from the aspiration inlet port;
   a distal portion terminating in an emulsifying tip, and providing an aspiration pathway terminating in an aspiration output, and at least one irrigation pathway terminating in at least one irrigation output; and
   a swivel ball provided at a base of the proximal portion and having a first opening to the irrigation fluidic pathway, and a second opening to the aspiration fluidic pathway, which seats within a socket cup provided at an upper end of the distal portion, wherein the socket cup provides an irrigation opening that fluidically connects the first opening and the at least one irrigation pathway, and an aspiration opening that fluidically connects the second opening and the aspiration pathway;
   wherein the swivel ball is capable of both an axial angular rotation and a circumferential rotation within the socket cup while maintaining continuous fluidic communication from the irrigation tubing inlet port to the at least one irrigation output, and from the aspiration tubing inlet port to the aspiration output;
   wherein the first opening and the second opening of the swivel ball, and the irrigation opening and the aspiration opening of the socket cup each exclusively comprise internal bores in the swivel ball and the socket cup extending from the first and second openings to their respective inlet ports.

2. The handpiece of claim 1, wherein the irrigation fluidic pathway at least partially comprises a reservoir.

3. The handpiece of claim 1, wherein the irrigation and aspiration tubing inlet ports comprise luer connectors.

4. The handpiece of claim 1, wherein the socket cup comprises alternating higher and low friction portions, so as to provide tactile feedback upon movement of the swivel ball.

5. The handpiece of claim 1, further comprising at least two seals capable of frictionally sealing against the swivel ball.

6. The handpiece of claim 5, wherein a first of the at least two seals seals the irrigation from leaking about the swivel ball.

7. The handpiece of claim 6, wherein a second of the at least two seals seal the aspiration from leaking about the swivel ball.

8. The handpiece of claim 7, wherein the second seal is more proximate to the distal portion than the first seal.

9. The handpiece of claim 6, wherein each of the seals comprises rubber, plastic, or silicon.

10. The handpiece of claim 6, wherein the first seal is at least substantially watertight.

11. The handpiece of claim 6, wherein the second seal is at least substantially airtight.

12. The handpiece of claim 1, wherein axial angular rotation of the swivel ball outside of a range of 10 to 90 degrees effectuates a first of the at least two seals breaking the continuous fluidic communication from the irrigation tubing inlet port to the at least one irrigation output.

13. The handpiece of claim 1, wherein circumferential rotation of the swivel ball outside of a range of 180 to 360 degrees effectuates a second of the at least two seals breaking the continuous fluidic communication from the aspiration tubing inlet port to the at least one aspiration output.

14. The handpiece of claim 1, further comprising a retainer that fastens over the swivel ball and onto an upper feature of the socket cup.

15. The handpiece of claim 14, wherein the retainer comprises a thread down, and wherein the upper feature comprises receiving threads.

16. The handpiece of claim 14, wherein the retainer comprises a screw down, and wherein the upper feature comprises screw-receiving holes.

17. The handpiece of claim 1, wherein the swivel ball comprises plastic.

18. The handpiece of claim 1, wherein the socket cup comprises plastic.

* * * * *